US009090637B2

(12) United States Patent
Thuilliez et al.

(10) Patent No.: US 9,090,637 B2
(45) Date of Patent: Jul. 28, 2015

(54) METHOD FOR SYNTHESISING A RARE EARTH ORGANOPHOSPHATE AND USE THEREOF TO PREPARE A "PREFORMED" CATALYTIC SYSTEM

(75) Inventors: Julien Thuilliez, La Roche Blanche (FR); Pierre Kiener, Gerzat (FR); Elodie Guerin, Saint-Ignat (FR)

(73) Assignees: COMPAGNIE GENERALE DES ETABLISSMENTS MICHELIN, Clermont Ferrand (FR); MICHELIN RECHERCHE ET TECHNIQUE S.A., Granges-Paccot (CH)

( * ) Notice: Subject to any disclaimer, the term of this patent is extended or adjusted under 35 U.S.C. 154(b) by 471 days.

(21) Appl. No.: 13/321,182

(22) PCT Filed: May 18, 2010

(86) PCT No.: PCT/EP2010/056836
§ 371 (c)(1),
(2), (4) Date: Feb. 3, 2012

(87) PCT Pub. No.: WO2010/133608
PCT Pub. Date: Nov. 25, 2010

(65) Prior Publication Data
US 2012/0130055 A1 May 24, 2012

(30) Foreign Application Priority Data
May 19, 2009 (FR) ...................................... 09 02426

(51) Int. Cl.
*C07F 9/11* (2006.01)
*A61K 6/04* (2006.01)
(52) U.S. Cl.
CPC .. *C07F 9/11* (2013.01); *A61K 6/043* (2013.01)
(58) Field of Classification Search
CPC .................................................. A61K 6/043
See application file for complete search history.

(56) References Cited

U.S. PATENT DOCUMENTS

| 5,220,045 | A | 6/1993 | Knauf et al. |
| 6,111,082 | A | 8/2000 | Yunlu et al. |
| 6,197,713 | B1 | 3/2001 | Lynch |
| 6,482,906 | B1 | 11/2002 | Tocchetto Pires et al. |
| 6,767,927 | B1 | 7/2004 | Yunlu et al. |
| 2004/0009870 | A1 | 1/2004 | Laubry |
| 2004/0019171 | A1 | 1/2004 | Laubry |
| 2005/0130835 | A1 | 6/2005 | Laubry et al. |
| 2010/0280264 | A1* | 11/2010 | Mathivet ........................ 556/24 |
| 2011/0009657 | A1 | 1/2011 | Thuilliez |

FOREIGN PATENT DOCUMENTS

| EP | 0924214 | 6/1999 |
| EP | 1509557 | 3/2005 |
| WO | WO 02/38635 | 5/2002 |
| WO | WO 02/38636 | 5/2002 |
| WO | WO 03/097708 | 11/2003 |
| WO | WO 2009/019100 | 2/2009 |
| WO | WO 2009/083480 | 7/2009 |

OTHER PUBLICATIONS

International Search Report (PCT/ISA/210) issued on Jul. 27, 2010, by European Patent Office as the International Searching Authority for International Application No. PCT/EP2010/056836.
Written Opinion (PCT/ISA/237) issued on Jul. 27, 2010, by European Patent Office as the International Searching Authority for International Application No. PCT/EP2010/056836.
E.V. Yurtov et al., Colloid Structures Formed in Extraction Systems With Organophosphorus Extractants, Proceedings of the International Solvent Extraction Conference, ISEC 2002, pp. 197-199.

* cited by examiner

*Primary Examiner* — Paul Dickinson
(74) *Attorney, Agent, or Firm* — Dickinson Wright PLLC

(57) ABSTRACT

The invention relates to a process for preparing a rare-earth organophosphate in the form of a fluid or not very viscous solution that can be used as is for the preparation of a "preformed" catalyst system intended, in particular, for the cis-1,4 stereospecific polymerization of conjugated dienes.

27 Claims, No Drawings

METHOD FOR SYNTHESISING A RARE EARTH ORGANOPHOSPHATE AND USE THEREOF TO PREPARE A "PREFORMED" CATALYTIC SYSTEM

The invention relates to a process for preparing a rare-earth organophosphate in the form of a solution that can be used as is in a catalyst system intended, in particular, for the cis-1,4 stereospecific polymerization of conjugated dienes.

In the 1980s, the first rare-earth-based catalyst systems saw the light of day and interest in them has been growing, on the one hand due to the non-toxicity of the metal and on the other hand due to the fact that non-aromatic solvents, such as hexane, cyclohexane, cuts of isomers of hexane or methylcyclohexane can be used as the polymerization solvent. More particularly, neodymium catalysis is currently experiencing a real expansion.

Rare-earth catalysts are multicomponent catalysts and are generally constituted of at least:
  a conjugated diene monomer,
  a salt of one or more rare-earth metals of an organic phosphoric acid or of an organic carboxylic acid,
  an alkylating agent constituted of an alkylaluminium corresponding to the formula $AlR_3$ or $HAlR_2$, and
  a halogen donor constituted of an alkylaluminium halide.

This type of catalyst is described, in particular, in International Patent Applications WO 02/38635, WO 02/38636 and WO 03/097708 in the name of the applicants.

Among the rare-earth salts, the rare-earth salts known as phosphates and of general formula $Ln[OP(=O)_x(OR)_{3-x}]_3$ (Ln being a metal from the lanthanide family, scandium or yttrium, x being equal to 1 or 2, R being identical or different, linear or branched, aliphatic or alicyclic alkyl radicals comprising 1 to 20 carbon atoms) are significant compounds for the preparation of highly active catalyst systems for the cis-1,4 stereospecific polymerization of conjugated dienes, more particularly butadiene and isoprene. These systems have the advantage of resulting in elastomers that have a narrow molecular weight distribution.

Due to their nature, these salts are not very soluble and have a high tendency to associate in a hydrocarbon solvent medium and generally result in the formation of gel, as described by Suglobov in document "DEHP Complexes of Lanthanides (III) and Actinides (III)", Journal of Alloys and Compounds, 213/214, 1994, p. 523-527). This leads to practical difficulties, whether during the synthesis thereof or the use thereof as a polymerization catalyst precursor.

Several methods of synthesis are described in the literature. Most consist of the reaction of a rare-earth salt of rare-earth halide or nitrate type with an organophosphate salt (Korovin et al., Russian Journal of Inorganic Chemistry, 22(5), 1977; Chen Tien et al. "Preparation and characterization of bis(2-ethylhexyl)phosphate ($P_{204}$) rare earth", K'o Hsuch T'ung Pao 1981, 26(13), 794-6; JP 60023406 in the name of Asahi, page 4).

Patent document EP 1 509 557 B1 in the name of the applicants describes the synthesis of a powder of neodymium tris(organophosphate) [$(RO)_2P(=O)O]_3Nd$ by reaction of:
  a) an aqueous solution of neodymium chloride $NdCl_3$ $(H_2O)_6$, prepared by reaction of HCl with $Nd_2O_3$, and
  b) a water/acetone solution of sodium di(2-ethylhexyl) phosphate.

This synthesis process, in several steps, allows a complete reaction and results in the formation of the neodymium tris [di(2-ethylhexyl)phosphate] salt in the form of a solid. After washing this solid with water a certain number of times, the qualitative test for the determination of chloride ions is almost negative, which indicates that an almost pure product is obtained. Once dry, the product is in the form of a pink-mauve powder.

Patent document U.S. Pat. No. 6,767,927 B1 describes a process for the synthesis, in three steps, of a stable solution of rare-earth tris(organophosphate) in a hydrocarbon solvent:
  1) preparation of an organophosphate salt by reaction of the corresponding acid and a base,
  2) reaction of the organophosphate obtained previously with a rare-earth salt,
  3) adjustment of the concentration of free acid.

This synthesis is carried out in a two-phase water/hydrocarbon solvent medium. At the end of the reaction, the water is removed by decantation and azeotropic distillation. The product of this synthesis process is a fluid solution that can be used directly for the preparation of a polymerization catalyst. Nevertheless, the process comprises a certain number of synthesis steps in order to result in the desired solution. This process furthermore generates aqueous effluents that contain ions, for example ammonium nitrate, which from an environmental point of view requires a supplementary step for the subsequent treatment of these waste products.

The preceding synthesis processes may be defined as being indirect processes. That is to say that the synthesis of the rare-earth phosphate salt is carried out starting from a rare-earth salt, obtained by reaction of the rare-earth oxide and an acid, and from an organophosphate salt, obtained by reaction of the corresponding acid and a base. The number of steps generally produces, for this type of process, complex and not very economical synthesis pathways. A drawback of these processes is that they generate aqueous waste products, which makes it necessary to introduce a supplementary step for treating these waste products.

Rare-earth tris(carboxylates), such as for example rare-earth versatates, are compounds that themselves can also be used as a precursor in the synthesis of catalysts for the cis-1,4 stereospecific polymerization. They can be synthesized according to the same pathway as before, that is to say by reaction of a carboxylate salt with a rare-earth salt (for example, reaction of sodium versatate with neodymium nitrate as described in patent document U.S. Pat. No. 6,111, 082).

Alternative synthesis pathways have been developed for the synthesis of organometallic salts of this family in order to reduce the cost of the synthesis by limiting the number of steps. In these syntheses, the carboxylate salt or the rare-earth salt is replaced by the precursor thereof, that is to say the corresponding carboxylic acid or the corresponding rare-earth oxide.

Patent document U.S. Pat. No. 6,482,906 B1 describes a process for preparing neodymium tris(neodecanoate) also known as neodymium tris(versatate), in four steps:
  1) preparing a sludge by dispersion of $Nd_2O_3$ in a hydrocarbon solvent and reaction with a deficiency of HCl relative to the neodymium,
  2) adding neodecanoic acid in an amount of 3.25 equivalents relative to the neodymium,
  3) settling of the reaction medium,
  4) separating the neodymium tris(neodecanoate) from the residual reactants.

This synthesis pathway has the advantage of not comprising the step of synthesis of the neodecanoate salt by reaction with a base, which removes one step. The drawback is that the reaction is not complete and that a step of separating the unreacted neodymium oxide from the solution of neodymium tris(neodecanoate) is necessary with a view to using the neodymium tris(neodecanoate) for other applications, especially for the preparation of a catalyst system.

Patent document U.S. Pat. No. 5,220,045 describes a process for the synthesis of neodymium neodecanoate in one step comprising the reaction, in a two-phase medium, of an aqueous solution of neodymium nitrate with an organic solution of versatic acid in the presence of a base of amine, ammonia or quaternary ammonium hydroxide type. During this synthesis, the ammonium neodecanoate salt is generated in situ in order to react with the neodymium nitrate. This synthesis pathway has the advantage of taking place in a single reactor and of being complete. It has the drawback of requiring the addition of a base to the reaction medium and of involving a certain number of washes with water and of decantation steps in order to rid the gel of its impurities, which is detrimental from an economical viewpoint. Furthermore, this process generates aqueous effluents that contain ions, for example ammonium nitrate, which, from the environmental point of view, requires a supplementary step for the subsequent treatment of these waste products.

Unlike the synthesis pathways described above, a direct synthesis consists in directly reacting the rare-earth oxide with the phosphoric or carboxylic acid, without an intermediate step of forming the rare-earth salt and/or the phosphate or carboxylate salt.

Patent EP 0 924 214 B1 relates to a process for fluidizing organic solutions of rare-earth compounds, such as rare-earth phosphates or carboxylates, by addition of a Lewis acid. Example 1 of this patent describes the preparation of lanthanum di(2-ethylhexyl)phosphate by reaction of lanthanum oxide $La_2O_3$ with di(2-ethylhexyl)phosphoric acid in hexane and a small amount of water. The mixture is stirred and brought to reflux until a clear yellow solution is obtained. The water is then removed by azeotropic distillation. The gel obtained is very viscous, the viscosities measured being greater than 90 000 cP, and has a brittle structure. Indeed, it is stated in this patent that holes (fracture zones) appear in the gel during the viscosity measurement. This gelatinous and "brittle" characteristic makes it difficult to handle such a product, especially during processing steps for the preparation of a catalyst system for the cis-1,4 stereospecific polymerization of conjugated dienes, and prevents its characterization. This involves taking precautions for the handling and characterization of this product, especially during the use of this gel in an industrial process.

The direct synthesis of a rare-earth organophosphate in solution in an organic solvent starting from an organophosphorus acid and a rare-earth compound is also described in document WO 2009/019100. The process for synthesizing this organophosphate has the distinctive feature of using a promoter chosen from water or certain acids, and makes it possible to prepare a solution of a rare-earth organophosphate having a low residual solids content and with an acceptable residual acidity. Nevertheless, the organophosphate solution prepared according to this claimed process may have an unsuitable viscosity and it may prove necessary to adjust its viscosity by adding an alcohol, a carboxylic acid or a phosphoric acid.

The objective of the present invention is to overcome the drawbacks encountered with the synthesis processes of the prior art. More particularly, one objective of the present invention is to propose a process for the synthesis of a rare-earth organophosphate comprising a minimum of steps, which should facilitate implementation on an industrial scale, and the product of which is free from residual rare-earth precursor. Another objective of the invention is to obtain rare-earth organophosphate solutions, the consistency of which is particularly suitable for processing with equipment suitable for low-viscosity products. Another objective of the invention is a synthesis of a rare-earth organophosphate which can be used directly and easily for a subsequent application, especially for the preparation of a catalyst system. Another objective of the invention is to implement a process that generates very few aqueous effluents that require a subsequent treatment in order to respond to an environmental problem.

This objective is achieved in that the inventors have just discovered, during their research, a method for the synthesis of a rare-earth organophosphate via a direct pathway, the product of which is, unexpectedly, free of residual rare-earth oxide or of any impurity, in amounts that are detrimental to any subsequent use. The direct synthesis process results in a product, the handling of which is not hindered either by a "brittle" character or by a high viscosity both of which would restrict the processing thereof with standard equipment and the use thereof during the preparation of a catalyst system for the cis-1,4 polymerization of conjugated dienes. The rare-earth organophosphate obtained via this process is in the form of a solution that is fluid or not very viscous, even when the neodymium weight content is high (for instance, up to 8%). Just as unexpectedly, it turns out that this solution can be easily used, as is, in particular as a precursor for a catalyst system intended for the cis-1,4 stereospecific polymerization of conjugated dienes without impairing the catalytic activity of the system or the characteristics of the polymer synthesized. The synthesis process according to the invention does not generate aqueous effluents that require subsequent treatment.

One subject of the invention is therefore a process for the synthesis, via a direct pathway, of a rare-earth organophosphate from the rare-earth oxide, an organophosphoric acid and a small amount of an organic or mineral acid in a single step.

The synthesis process of the invention that makes it possible to prepare a rare-earth organophosphate is a direct synthesis process which comprises:
   the dispersion, under high shear, of a rare-earth oxide in a medium comprising at least one organic solvent, water, an organophosphoric acid and a small amount of an organic or mineral acid, and simultaneously or sequentially
   the reaction of the rare-earth oxide with the organophosphoric acid and the small amount of organic or mineral acid.

The high shear dispersion according to the invention may be carried out by any suitable means using any dynamic mixer known to a person skilled in the art. Particularly suitable are the devices constituted of a rotating stirrer comprising one or more impellers fixed to a shaft, which dissipate power densities of the order of 0.1 to 250 kW/m$^3$/unit of dynamic viscosity of the reaction mixture, more particularly of the order of 1 to 150 kW/m$^3$/Pa·s. The shear depends on the characteristics of the impeller, in particular on its geometry. Devices of this type are, for example, rotor/stator mixers, especially those sold by VMI Rayneri under the trademark "Ultramix" and by IKA under the trademark "Ultra Turrax".

The expression "high shear" should be understood to mean a "high shear rate" or a "high velocity gradient", which are two synonymous expressions for a person skilled in the art. The term "high" is understood, in the present case, to mean high enough to attain the desired properties of the rare-earth organophosphates prepared according to the process of the invention.

The concept of "average velocity gradient" in a stirred chamber is defined, for example, in the article "Agitation Mélange—concepts théoriques de base" [Stirring/Mixing—basic theoretical concepts], written by Michel Roustan, Jean-Claude Pharamond and Alain Line from the work "Techniques de l' ingénieur, traité Génie des Procédés [Engineering Techniques, treatise on Process Engineering]—J3 800, page 13". This concept is, for example, used in patent U.S. Pat. No. 6,638,918, which describes it in the same manner as in the preceding reference. Thus, the average shear ($\Gamma_{average}$) in the medium can be expressed by the equation:

$$\Gamma_{average} = kN$$

in which k is a proportionality constant which depends on the type of mixer blade and on the configuration of the chamber of the mixer and N is the speed of the agitator impellers (in $s^{-1}$). $\Gamma_{average}$ is expressed in $s^{-1}$. The mixers that can be used for carrying out the process according to the invention have a constant k that varies between 10 and 13.

Associated with this concept of shear is a blade tip peripheral speed, expressed by the equation:

$$V_{periph} = \pi ND$$

in which D is the diameter of the agitator impellers expressed in meters and N is their rotational speed expressed in $s^{-1}$.

According to the invention, the expression "high shear dispersion" is understood to mean a dispersion carried out with stirring at high blade tip speed, typically greater than 4 m·$s^{-1}$, preferably greater than or equal to 10 m·$s^{-1}$, and more preferably still between 10 m·$s^{-1}$ and 50 m·$s^{-1}$, which gives the medium a shear typically greater than 200 $s^{-1}$, preferably between 200 $s^{-1}$ and 50 000 $s^{-1}$ and more preferably still between 200 $s^{-1}$ and 20 000 $s^{-1}$.

As a function of the desired shear level, a person skilled in the art will know how to use a stirring system that has a suitable geometry and how to apply it at a sufficient rotational speed to achieve the desired blade tip rotational speed and shear level. Depending on the nature of the stirring system and the size of the synthesis reactor, the rotational speed may, by way of example, be between 100 rpm and 30 000 rpm.

The temperature of the medium during the high shear dispersion of the rare-earth oxide in this medium and the reaction of the rare-earth oxide with the organophosphoric acid and the organic or mineral acid is defined as a function of the nature of the solvents used and of the total amount of phosphoric acid introduced into the medium. The temperature of the medium is generally between 0 and 130° C. This temperature is preferably between 20 and 110° C. and more preferably still between 20 and 90° C.

The duration of the dispersion of the rare-earth oxide in the medium may vary from 1 to 100 minutes; preferably it is from 1 to 60 minutes. The total duration of the synthesis comprising in particular the step of dispersing the rare-earth oxide and the step of reacting the rare-earth oxide with the organophosphoric acid and the organic or mineral acid is from 1 to 600 minutes.

According to the invention, the expression "rare earth" is understood to mean a metal chosen from yttrium, scandium and the lanthanides, metals that have an atomic number ranging from 57 to 71 inclusive in Mendeleev's periodic table of the elements. Preferably, the rare-earth metal is chosen from lanthanides such as, in particular, lanthanum, praseodymium, gadolinium or neodymium, neodymium being more particularly preferred.

Although the process of the invention also applies to yttrium and scandium, the invention will be described in the following paragraph by reference to lanthanides for reasons of simplification of writing.

One of the reactants of the process of the invention is lanthanide oxide. According to the invention, the expression "lanthanide oxide" is understood to mean any species of lanthanide sesquioxide type corresponding to the formula $Ln_2O_3$, but also any partially or completely hydrated form of lanthanide oxide containing Ln-OH functions. Indeed, due to their hygroscopic character, lanthanide oxides may absorb a certain amount of water under the effect of the humidity of the ambient air. This water may lead to the hydration of the lanthanide oxide and to the formation of other lanthanide-based species, such as lanthanide trihydroxide, according to the equation:

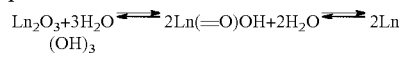

By way of illustration, in the case where the lanthanide metal is neodymium, the theoretical neodymium weight content of neodymium sesquioxide, denoted by % Nd $[Nd_2O_3]_{theo}$, is 85.74%. The theoretical neodymium weight content of neodymium trihydroxide, denoted by % Nd[Nd $(OH)_3]_{theo}$, is 73.87%.

The neodymium weight content of the raw material used, denoted by % Nd[$Nd_2O_3$], is determined according to any characterization method known to a person skilled in the art. For example, the assay methods described in patent application WO 03/097708 in the name of the applicants may be used.

Thus, the degree of hydration $D_{hydration}$ of a lanthanide oxide is defined as being:

$$D_{Hydration} = \frac{\% \ Nd[Nd_2O_3] - \% \ Nd[Nd(OH)_3]_{theo}}{\% \ Nd[Nd_2O_3]_{theo} - \% \ Nd[Nd(OH)_3]_{theo}}$$

Thus, the degree of hydration $D_{hydration}$ according to the invention of pure neodymium sesquioxide of formula $Nd_2O_3$ is 0%, whilst the degree of hydration of neodymium trihydroxide of formula $Nd(OH)_3$ is 100%.

Preferably, the synthesis process according to the invention involves a rare-earth oxide having a degree of hydration ranging from 0 to 100%, preferably between 0 and 50% and more preferably still between 0 and 20%.

The organophosphoric acid, the second reactant of the process according to the invention, is chosen from the following compounds: phosphoric acid diesters of general formula (RO)(R'O)PO(OH), in which R is an alkyl, aryl or alkylaryl radical and R' is an alkyl, aryl or alkylaryl radical; phosphoric acid monoesters of general formula $(RO)PO(OH)_2$ in which R is an alkyl, aryl or alkylaryl radical; phosphonates of general formula (RO)R'P(O) or $RP(O)(OH)_2$ in which R is an alkyl, aryl or alkylaryl radical; phosphinates of general formula R(R')P(O)OH or R(H)P(O)OH in which R is an alkyl, aryl or alkylaryl radical; and mixtures thereof.

Preferably, the organophosphoric acid is chosen from phosphoric acid diesters of general formula (RO)(R'O)PO (OH), in which R is an n-butyl, isobutyl, pentyl, amyl, isopentyl, 2,2-dimethylhexyl, 1-ethylhexyl, 2-ethylhexyl, tolyl, nonylphenoxy radical and R' is an n-butyl, isobutyl, pentyl, amyl, isopentyl, 2,2-dimethylhexyl, 2-ethylhexyl, 1-ethylhexyl, tolyl, nonylphenoxy radical; phosphoric acid monoesters of general formula $(RO)PO(OH)_2$ in which R is an n-butyl, isobutyl, pentyl, amyl, isopentyl, 2,2-dimethylhexyl, 1-ethylhexyl, 2-ethylhexyl, tolyl, nonylphenoxy radical; phosphonates of general formula (RO)R'P(O) or RP(O)(OH)$_2$ in which R is an n-butyl, isobutyl, pentyl, amyl, isopentyl, 2,2-dimethylhexyl, 2-ethylhexyl, 1-ethylhexyl, tolyl, nonylphenoxy radical; phosphinates of general formula R(R')P(O)OH or R(H)P(O)OH in which R is an n-butyl, isobutyl, pentyl, amyl, isopentyl, 2,2-dimethylhexyl, 2-ethylhexyl, 1-ethylhexyl, tolyl, nonylphenoxy radical; and mixtures thereof. More preferably still, the organophosphoric acid according to the invention is chosen from di(2-ethylhexyl)phosphoric acid.

The molar ratio of the organophosphoric acid to the rare earth is a function of the nature of the organophosphoric acid. A person skilled in the art will adjust the amount of organophosphoric acid to be introduced into the medium as a function of its nature.

When the organophosphoric acid is a phosphoric acid diester, the molar ratio of the organophosphoric acid to the rare earth is from 2.7 to 4, preferably from 2.75 to 3.5 and more preferably still from 2.8 to 3.3.

The organic or mineral acid, third reactant of the process according to the invention, is chosen from organic or mineral acids having a pK$_a$ at 25° C. of less than 2.5, preferably ranging from −10 to 2.5, more preferably still −1 to 2, and mixtures thereof.

Preferably, the mineral or organic acid is chosen from the following compounds: perchloric acid HClO$_4$, chloric acid HClO$_3$, chlorous acid HClO$_2$, hydrochloric acid HCl, bromic acid HBrO$_3$, hydrobromic acid HBr, iodic acid HIO$_3$, periodic acid HIO$_4$, orthoperiodic acid H$_5$IO$_6$, hydroiodic acid HI, trichloroacetic acid CCl$_3$—COOH, dichloroacetic acid CCl$_2$H—COOH, trifluoroacetic acid CF$_3$COOH, nitric acid HNO$_3$, peroxonitric acid HNO$_4$, sulphurous acid H$_2$SO$_3$, sulphuric acid H$_2$SO$_4$, lithium, sodium or potassium hydrogen sulphates, fluorosulphuric acid FSO$_3$H, sulphonic acid HSO$_3$H, trifluoromethanesulphonic acid CF$_3$—SO$_3$H, benzenesulphonic acid, naphthalenesulphonic acid, phosphoric acid H$_3$PO$_4$, lithium, sodium or potassium hydrogen phosphates, phosphoric acid monoesters (RO)P(=O)(OH)$_2$, monoesters of phosphinate type of formula (R)PH(=O)OH, pyrophosphoric acid H$_4$P$_2$O$_7$, phosphorous acid H$_3$PO$_3$, hypophosphorous acid H$_3$PO$_2$, chromic acid H$_2$CrO$_4$, picric acid, maleic acid, oxalic acid and mixtures thereof.

More preferably still, the mineral or organic acid is chosen from the following compounds: hydrochloric acid HCl, trichloroacetic acid CCl$_3$—COOH, trifluoroacetic acid CF$_3$COOH, nitric acid HNO$_3$, sulphuric acid H$_2$SO$_4$, lithium, sodium or potassium hydrogen sulphates, phosphoric acid monoesters (RO)P(=O)(OH)$_2$, monoesters of phosphinate type of formula (R)PH(=O)OH, trifluoromethanesulphonic acid CF$_3$—SO$_3$H, phosphorous acid H$_3$PO$_3$ or hypophosphorous acid H$_3$PO$_2$ and mixtures thereof. According to one particularly preferred variant of the invention, hydrochloric acid or nitric acid is chosen from among the mineral acids.

In order not to hinder the subsequent use of the rare-earth organophosphate solution in a catalyst for the polymerization of conjugated dienes, a small amount of organic or mineral acid is used in the process according to the invention. The expression "small amount" is understood according to the invention to mean an amount such that the molar ratio of the organic or mineral acid with respect to the rare earth is between 0 and 0.25 equivalents (the limits of this interval being excluded), preferably the molar ratio has a value ranging from 0.03 to 0.20 equivalents (the limits being included).

The molar ratio of the total amount of acids in the medium to the rare earth is a function of the nature of the organophosphoric acid and of the mineral or organic acid. The expression "the total amount of acids in the medium" is understood to mean the sum of the amount of organophosphoric acid and mineral or organic acid according to the invention. A person skilled in the art will adjust the amount to be introduced into the medium as a function of the nature of the acids present in the medium. Thus, advantageously, the total amount of acids in the medium is chosen so that the molar ratio of the total amount of acids with respect to the rare earth is between 2.70 and 4.25. Preferably, this molar ratio is between 2.78 and 3.68 and more preferably still between 2.85 and 3.45.

The molar ratio of the organic or mineral acid to the rare earth is a function of its nature, and also of the nature of the organophosphoric acid and of the molar ratio of the latter with respect to the rare earth. A person skilled in the art will adjust this amount of organic or mineral acid to be introduced into the medium as a function of the nature and of the amount of the chosen reactants.

The organic or mineral acid according to the invention is introduced into the reaction medium in pure form or in the form of an aqueous solution. In the latter case, the organic or mineral acid according to the invention is introduced either in the form of a concentrated aqueous solution, or diluted in the amount of water introduced at the very start of the synthesis.

The organic or mineral acid according to the invention is introduced alone or as a mixture with one or more other organic or mineral acids according to the invention.

According to the process of the invention, the medium comprises at least one organic solvent. The expression "organic solvent" is understood to mean, within the context of the invention, one or more solvents comprising at least one inert hydrocarbon solvent. According to one preferred embodiment of the invention, the inert hydrocarbon solvent is an aliphatic and alicyclic solvent of low molecular weight such as, by way of indication, n-pentane, iso-pentane, cyclopentane, a cut of pentane isomers, a cut of C5 compounds, a C5 cut from the steam cracking of naphtha, hexane, cyclohexane, a cut of hexane isomers, methylcyclohexane, heptane, isomers thereof or a mixture of these solvents. More preferably still, use is made of n-pentane, a cut of C5 compounds, cyclohexane, methylcyclohexane or a mixture thereof as inert hydrocarbon solvents.

According to one preferred implementation of the invention, the volume ratio of water relative to the inert hydrocarbon solvent is strictly greater than 0 and strictly less than 1.

According to one variant of the process of the invention, the medium may also comprise other components capable of acting on the implementation of the process or else on the properties of the product obtained.

According to one variant of the synthesis process of the invention, the steps of high shear dispersion of the rare-earth oxide in the medium and of reaction of the rare-earth oxide with the organophosphoric acid and the organic or mineral acid may be carried out in one and the same reactor ("one-pot" synthesis). In this case, the dispersion of the rare-earth oxide in the reaction medium and the reaction of the rare-earth oxide with the organophosphoric acid and the organic or mineral acid may take place simultaneously or sequentially. In this case, the high shear stirring is activated only for the period of time needed for the dispersion.

According to another variant of the synthesis process of the invention, the steps of high shear dispersion of the rare-earth oxide in the medium and of reaction of the rare-earth oxide with the organophosphoric acid and the organic or mineral acid may be carried out in two different reactors. After the high shear dispersion of the rare-earth oxide in the medium, the mixture is transferred into a second reactor. This second reactor may be equipped with a conventional blade-type mechanical stirring system and the reaction is carried out with moderate mechanical stirring. The medium in the two reactors is generally heated at a temperature from 0 to 100° C. for a total duration of the process that varies from 1 to 400 minutes. According to this variant, the steps of the process of the invention may take place sequentially or simultaneously, the reaction of the rare-earth oxide with the organophosphoric acid and the organic or mineral acid possibly, for example, having started during the high shear dispersion of the rare-earth oxide in the medium, in the first reactor, and being continued in the second reactor.

After reaction of the phosphoric acid and the organic or mineral acid with the rare-earth oxide, the rare-earth organophosphate solution obtained comprises water and must therefore be dried, in particular in view of the subsequent use of the rare-earth organophosphate solution for the preparation of a catalyst for the polymerization of conjugated dienes. This removal may be carried out by any process known to a person skilled in the art. According to one preferred variant of the invention, the water is removed by azeotropic distillation.

The implementation of the process of the invention allows the synthesis of a rare-earth organophosphate in the form of a fluid or not very viscous solution with a high degree of conversion of the rare-earth oxide. No supplementary washing or purification step is necessary. This does not however rule out such steps, while remaining within the scope of the invention. When such a supplementary washing or purification step is carried out, the implementation of a subsequent treatment of the aqueous waste products is not necessary, since these are either free of any by-product of the reaction, or can be recycled to the synthesis process.

Specifically, according to another variant of the synthesis process of the invention, an optional step of washing the rare-earth organophosphate solution is carried out immediately after the reaction of the phosphoric acid and the organic or mineral acid with the rare-earth oxide. This washing step consists in introducing into the medium, comprising the rare-earth organophosphate, a supplementary volume of water, then in stirring the thus resulting two-phase medium so as to wash the solution, then finally in separating, by any method known to a person skilled in the art, the aqueous phase from the rare-earth organophosphate organic solution. This washing step makes it possible, in particular, to remove the excess reactants that have not reacted, such as for example the organophosphoric acid and water-soluble ionic species arising from the organic or mineral acid. A person skilled in the art will adjust the washing conditions, in terms of the volume of water used, stirring conditions used and number of consecutive washing operations in order to achieve the desired characteristics of the product.

This additional amount of water must be removed at the end of the washing operation, in particular in view of the subsequent use of the rare-earth organophosphate solution for preparing a catalyst for the polymerization of conjugated dienes. This amount of water may optionally be recycled upstream of the synthesis process, so as to reuse the organophosphoric acid, such as the di(2-ethylhexyl)phosphoric acid, that has not reacted.

The solution obtained by the synthesis process of the invention comprises at least one rare-earth organophosphate and an inert hydrocarbon solvent as defined previously. It may also comprise one or more residual free acids, and also a small amount of water.

According to one preferred variant, the process of the invention allows the synthesis of a lanthanide organophosphate, and more particularly a neodymium organophosphate in the form of a fluid or not very viscous solution. The synthesis, in accordance with the process of the invention, of neodymium tris[di(2-ethylhexyl)phosphate] constitutes one particularly preferred aspect of this variant.

The neodymium organophosphate solution obtained preferably by the implementation of the synthesis process according to the invention advantageously has, prior to any subsequent treatment, the following characteristics:
  the weight content of Nd is between 2.2 and 8.5%, preferably between 2.3 and 8%;
  a residual acidity in the solution of between 0 and 25 mmol per 100 g of salt and preferably of between 1 and 15 mmol per 100 g of salt;
  a viscosity of between 200 and 40 000 cP, preferably of between 1000 and 20 000 cP.

This neodymium organophosphate solution also preferably has the following characteristics:
  the amount of residual water in the solution is less than 500 ppm, preferably less than 200 ppm and more preferably still less than 100 ppm;
  the molar excess of organophosphoric acid with respect to neodymium has a value ranging from 0 to 100%, preferably from 0 to 50% and more preferably still from 0 to 30%.

The rare-earth organophosphate solution obtained by the process according to the invention may advantageously be used as is or it may undergo modifications after its preparation and before any subsequent use, without this departing from the scope of the invention. In the present application, the term "modification" is understood to mean any treatment that the solution obtained directly by the process of the invention could undergo, for example the removal of all or some of the residual free acid by any method known to a person skilled in the art, such as, in particular, washing with an aqueous solution, washing with an aqueous solution containing a base, such as ammonium hydroxide or sodium hydroxide, washing with an aqueous solution containing an acid or else the addition of various agents, such as for example certain aluminium derivatives corresponding to the formula $Al(R)_{3-n}H_n$, where n has the value 0, 1 or 2 and R is a hydrocarbon comprising 1 to to 8 carbon atoms, such as for example, in particular, triethylaluminium, triisobutylaluminium, trioctylaluminium or else diisobutylaluminium hydride.

The rare-earth organophosphate solution obtained by the process according to the invention may be used as is, for example for the preparation of catalyst systems for the stereospecific polymerization of conjugated dienes. In particular, it may be used as is, together with an alkylating agent, for example an alkyl aluminium, and together with a halogen donor, for example a dialkylaluminium chloride, without this being detrimental to the preparation of the catalyst, to its activity or to the characteristics of the prepared polymer.

Thus, another subject of the invention is the preparation of a "preformed" catalyst system for the stereospecific polymerization of conjugated dienes based on at least:
  a conjugated diene monomer,
  the rare-earth organophosphate solution described previously,
  an alkylating agent constituted of an alkylaluminium of formula $AlR_3$ or $HAlR_2$ and
  a halogen donor which belongs to the family of alkylaluminium halides with the exclusion of alkylaluminium sesquihalides,
which comprises the steps of preparing the rare-earth organophosphate solution, particularly neodymium tris(organophosphate) according to the process in accordance with the invention described above.

This process is carried out without impairment linked to the nature of the rare-earth organophosphate and/or to its production process.

More particularly, the process for preparing this "preformed" catalyst system according to the invention implements the following steps:

in a first step, the rare-earth organophosphate solution, more particularly the neodymium organophosphate is prepared according to the process described above;

in a second step, a conjugated diene monomer is added to the rare-earth organophosphate solution obtained;

in a third step, an alkylating agent is added to the solution obtained at the end of the second step in order to obtain an alkylated salt; and in a fourth step, a halogen donor is added to the alkylated salt obtained previously.

The conjugated diene monomers, the alkylating agents and the halogen donors that can be used within the context of the process for preparation of the catalyst system of the invention are as defined, in particular, in patent EP 1 509 557 B1 in the name of the applicants.

The catalyst system according to the invention is particularly suitable for the cis-1,4 stereospecific polymerization of conjugated dienes, in particular of butadiene and of isoprene, in continuous mode or in batch mode.

The process for polymerization of conjugated dienes consists in reacting at least one conjugated diene monomer in the presence of the catalyst system of the invention in an inert hydrocarbon polymerization solvent, for example cyclohexane, methylcyclohexane or mixture thereof. This process is preferably carried out at a temperature ranging from 0° C. to 100° C.

The polymer thus prepared has a high content of cis-1,4 units, preferably greater than 97%, and a macrostructure that has a narrow molar mass distribution.

By way of example, mention may be made of the preparation of polybutadiene by batch polymerization with a catalyst system based on neodymium organophosphate of the invention, having a polydispersity index Ip, measured by the "SEC" technique, of less than 2, or else the batch preparation of polyisoprene having a polydispersity index of less than 2.7. Continuous polymerization with the same catalyst system makes it possible to obtain polybutadiene and polyisoprene having Ip values of less than 2.7 and 3.5 respectively.

The aforementioned features of the present invention, and also other features, will be better understood on reading the following description of several exemplary embodiments of the invention, given by way of illustration and non-limitingly, and also the diagram which represents the catalytic activity of catalyst systems in accordance with the invention and of catalyst systems of the prior art, evaluated by measuring the conversion rate of the monomer to polymer as a function of the reaction time.

I. Synthesis of Organic Phosphate Salts of Neodymium

Neodymium tris(di(2-ethylhexyl)phosphate) was synthesized. The synthesis conditions which are explained in detail below were used for each test.

Raw Materials

1—Neodymium Oxide

A neodymium oxide with a weight content of neodymium equal to 73.6% (type A) or a neodymium oxide with a weight content of neodymium equal to 82.4 wt % (type B) is used.

2—Organic or Mineral Acids

The acid compounds were obtained from Sigma-Aldrich and were used in the form of an aqueous solution having a concentration between 3 and 5 mol/L.

3—Other Reactants

Di(2-ethylhexyl)phosphoric acid, cyclohexane, methylcyclohexane and the other reactants were obtained from Sigma-Aldrich, Acros Organics, Crompton, Fluka and Sigma-Aldrich.

Characterization Techniques.

1—Nd and P Assay

The weight contents of neodymium and of phosphorus are determined by elemental analyses via complexometry.

2—Free Acid Species Assay

The amount of residual free acids is determined by potentiometric assay via acid-base reaction.

3—Water Assay

The Karl Fischer method is used.

4—Content of Insoluble Species

The amount of insoluble species present in the neodymium tris(di(2-ethylhexyl)phosphate) gel or solution is determined by centrifuging the gel or solution at a temperature of 20° C. at a speed of 3500 rpm and is expressed as a weight percentage of solid relative to the gel or solution.

5—Measurement of the Viscosity of neodymium tris(di(2-ethylhexyl)-phosphate)

The equipment used for determining the viscosity of the solution is a "Haake" brand, "Rheostress 1" model, imposed-stress rheometer. The plates used are either of plate-plate type (35 mm diameter) or cone-plate type (60 mm diameter). The gap between the upper rotor and the lower rotor is typically 0.5 mm. The measurement temperature is 30° C. The viscosity value is determined for a shear rate of $1\ s^{-1}$. The viscosity measured is expressed in cP (centipoise).

1) Synthesis of an Organic Phosphate Salt of Neodymium According to the Process Described in Patent EP 0 924 921 B1:

The following counterexamples make it possible to demonstrate the advantage of high shear stirring.

Counterexample 1

Introduced into a jacketed 1-liter reactor equipped with a Dean-Stark trap, a condenser and a blade-type mechanical stirring system were 15.59 g of $Nd_2O_3$ of type A (0.040 mol), 83.8 g of di(2-ethylhexyl)phosphoric acid (DEHPA) (0.249 mol), 560 ml of methylcyclohexane and 20 ml of water. The mixture was brought to reflux and stirred for 300 minutes. The presence of a solid in suspension was observed. The water of the medium was then removed by azeotropic distillation. After decanting from the reactor, 490 g were obtained of a viscous and brittle cloudy gel which had solid particles in suspension. The solid could not be separated from the gel by centrifuging, due to the viscosity of the gel being too high.

This test shows that the synthesis conditions described in Example 1 of patent EP 0 924 214 B1, applied to neodymium oxide and to an alicyclic solvent, do not make it possible to obtain a tris(organophosphate) gel that is clear and free of solid residue in suspension.

Counterexample 2

Introduced into a jacketed 1-liter reactor equipped with a Dean-Stark trap, a condenser and a blade-type mechanical stirring system were 13.99 g of $Nd_2O_3$ of type B (0.040 mol), 83.8 g of di(2-ethylhexyl)phosphoric acid (DEHPA) (0.249 mol), 560 ml of methylcyclohexane and 20 ml of water. The mixture was brought to reflux and stirred for 300 mixtures. The presence of a solid in suspension was observed. The water of the medium was then removed by azeotropic distillation. After decanting from the reactor, 497 g were obtained of a viscous and brittle gel which had a solid in suspension. The solid could not be separated from the gel by centrifuging, due to the viscosity of the gel being too high.

This test shows that the synthesis conditions described in Example 1 of patent EP 0 924 214 B1, applied to neodymium oxide and to an alicyclic solvent, do not make it possible to obtain a tris(organophosphate) gel that is clear and free of solid residue in suspension.

Counterexample 3

Introduced into a jacketed 1-liter reactor equipped with a Dean-Stark trap, a condenser and a blade-type mechanical stirring system were 15.59 g of $Nd_2O_3$ of type A (0.040 mol), 92.3 g of di(2-ethylhexyl)phosphoric acid (DEHPA) (0.275 mol), 550 ml of methylcyclohexane and 20 ml of water. The mixture was brought to reflux and stirred for 120 minutes. The presence of a solid in suspension was observed. The water of the medium was then removed by azeotropic distillation. After decanting from the reactor, 480 g were obtained of a gel having a solid in suspension (weight content of solid=0.3%).

This test shows, by fluidizing the gel obtained for better centrifugation owing to the addition of a supplementary amount of DEHPA, that the gel contains a sizeable amount of residual solid.

All of these examples show that the synthesis conditions described in patent document EP 0 924 214 B1, applied to neodymium metal and to an alicyclic solvent, do not make it possible to obtain a clear neodymium organophosphate solution that is not very viscous and is even fluid.

3) Synthesis of an Organic Phosphate Salt of Neodymium According to the Process of the Invention:

Example 1

Introduced into a 1-liter beaker were 15.83 g of $Nd_2O_3$ (0.090 mol of Nd), 94.78 g of di(2-ethylhexyl)phosphoric acid (DEHPA) (0.288 mol), 505 g of cyclohexane and 21 ml of water. The mixture then underwent treatment with a rotor-stator of Ultra-Turrax brand at a speed of 3000 rpm so as to disperse the neodymium oxide in the medium. From the start of the treatment with the rotor-stator, 0.0162 mol of concentrated hydrochloric acid HCl, i.e. 0.18 equivalents with respect to the neodymium, was added in the form of a concentrated aqueous solution. The treatment was carried out for a duration of 20 minutes. The medium was then transferred to a jacketed 1-liter reactor equipped with a Dean-Stark trap, a condenser and a blade-type mechanical stirring system. The mixture was brought to boiling and the water of the medium was removed by azeotropic distillation. After decanting from the reactor, a fluid and translucent violet solution was obtained, the characteristics of which are presented in Table 1.

Example 2

The procedure was the same as that in Example 1, except that the amount of hydrochloric acid was replaced by 0.054 mol of concentrated nitric acid $HNO_3$, i.e. 0.06 equivalents with respect to the neodymium. A fluid and translucent violet solution was obtained, the characteristics of which are presented in Table 1.

Example 3

Introduced into a 1-liter beaker were 57.07 g of $Nd_2O_3$ (0.324 mol of Nd), 318.57 g of di(2-ethylhexyl)phosphoric acid (DEHPA) (0.968 mol), 241 g of cyclohexane and 10 ml of water. The mixture then underwent treatment with a rotor-stator of Ultra-Turrax brand at a speed of 3000 rpm so as to disperse the neodymium oxide in the medium. From the start of the treatment with the rotor-stator, 0.0648 mol of nitric acid $HNO_3$, i.e. 0.20 equivalents with respect to the neodymium, was added in the form of a concentrated aqueous solution. The treatment was carried out for a duration of 30 minutes. The medium was then transferred to a jacketed 1-liter reactor equipped with a Dean-Stark trap, a condenser and a blade-type mechanical stirring system. The mixture was brought to reflux for a duration of 210 minutes, then the water of the medium was removed by azeotropic distillation. After decanting from the reactor, a fluid and translucent violet solution was obtained, the characteristics of which are presented in Table 1.

Example 4

The procedure was the same as that in Example 3, except that the amount of nitric acid was replaced by 0.0648 mol of concentrated hydrochloric acid HCl, i.e. 0.20 equivalents with respect to the neodymium. A fluid and translucent violet solution was obtained, the characteristics of which are presented in Table 1.

TABLE 1

|  | C.-Ex. 1 | C.-Ex. 2 | C.-Ex. 3 | Ex. 1 | Ex. 2 | Ex. 3 | Ex. 4 |
| --- | --- | --- | --- | --- | --- | --- | --- |
| Initial DEHPA/Nd stoichiometry | 3.12 | 3.12 | 3.44 | 3.20 | 3.20 | 3.00 | 3.02 |
| Mineral or organic acid used | — | — | — | HCl | $HNO_3$ | $HNO_3$ | HCl |
| Acid/neodymium molar ratio | — | — | — | 0.18 | 0.06 | 0.20 | 0.20 |
| Apparatus used for the dispersion | No | No | No | Trimix | Trimix | Trimix | Trimix |
| Diameter of the impeller (m) | 0.04 | 0.04 | 0.04 | 0.069 | 0.069 | 0.069 | 0.069 |
| Rotational speed (rpm) | 8.3 | 8.3 | 8.3 | 50 | 50 | 50 | 50 |
| Blade tip peripheral speed (m · s$^{-1}$) | 1 | 1 | 1 | 10.7 | 10.7 | 10.7 | 10.7 |
| Shear calculated with k = 10 (s$^{-1}$) | 83 | 83 | 83 | 500 | 500 | 500 | 500 |
| Dispersion time in minutes | — | — | — | 20 | 20 | 30 | 30 |
| Reflux time in minutes | 300 | 300 | 120 | 0 | 0 | 210 | 240 |
| Azeotropic distillation time in minutes | 180 | 180 | 180 | 350 | 350 | 300 | 240 |
| Total duration of the synthesis in minutes | 480 | 480 | 400 | 370 | 370 | 540 | 510 |
| Appearance of the salt | Cloudy | Cloudy | Cloudy | Clear | Clear | Clear | Clear |
| Presence of solid | yes | yes | yes | No | No | No | No |
| Content of insoluble species | nd | nd | 0.3% | 0% | 1'0% | 0% | 0% |
| % Nd | 2.42% | 2.34% | 2.26% | 2.61% | 2.43% | 7.52% | 7.13% |
| % P | nd | nd | nd | 1.82% | 1.73% | 4.81% | 4.62% |

TABLE 1-continued

|  | C.-Ex. 1 | C.-Ex. 2 | C.-Ex. 3 | Ex. 1 | Ex. 2 | Ex. 3 | Ex. 4 |
|---|---|---|---|---|---|---|---|
| Free acidity in mmol per 100 g of salt | 5.6 | 5.1 | 11.7 | 5.2 | 4.3 | 11.4 | 9.0 |
| Viscosity in cP | 92 000 | 96 000 | 34 000 | 9 000 | 8 000 | 2 000 | 4 000 | nd: value not determined

II Preparation of Catalyst Systems
Synthesis of "Control" Catalyst Systems and Catalyst Systems According to the Invention from these Salts:

In view of obtaining each catalyst system, the corresponding salt of neodymium in gel or solution form was poured into a reactor that had previously been cleaned of its impurities. The control gel was prepared according to patent U.S. Pat. No. 6,767,927. The solutions according to the invention were those prepared in the preceding examples.

First Step of "Preforming" Each Catalyst System:

Introduced next, into the reactor at a temperature of 30° C., were butadiene and also a certain amount of the inert hydrocarbon solvent of the synthesis of the neodymium salt.

Second Step of Alkylation:

Introduced next into the reactor was diisobutylaluminium hydride (HDiBA) as an alkylating agent of the neodymium salt, at a concentration of around 1M. The alkylation time was 15 min. The temperature of the alkylation reaction was equal to 30° C.

Third Step of Halogenation:

Introduced next into the reactor was diethylaluminium chloride (CDEA) as a halogen donor, at a concentration of around 1M. The temperature of the medium was brought to 60° C. The halogenation time was 70 minutes.

Fourth Step of Ageing:

An ageing of the mixture thus obtained was then carried out by maintaining this temperature of 60° C. for a time of 120 min.

Finally, the catalyst solution, under a nitrogen atmosphere, was stored in a freezer at a temperature of −15° C.

The molar ratios of the various constituents (butadiene, alkylating agent and halogen donor) relative to the neodymium salt of the catalyst systems thus prepared are given in the following tables.

These catalyst systems were then tested in the polymerization of butadiene in accordance with the processes described below.

III. Polymerization of Butadiene Using the Prepared Catalyst Systems:

The polymer characterization techniques are described in Appendix 1.

1) Polymerization Procedure:

A 250 ml "Steinie" bottle, previously washed and dried, and equipped with pierced caps and with a rubber septum was used as a polymerization reactor. Each butadiene polymerization reaction was carried out under an inert (nitrogen) atmosphere.

For each polymerization, 122 ml of methylcyclohexane was introduced into said bottle as a polymerization solvent. This methylcyclohexane was sparged with nitrogen for 10 minutes in order to remove the impurities.

16 ml (10.4 g) of freshly distilled butadiene was then introduced into the bottle using a syringe.

An amount of 582 µmol of HDiBA per 100 g of butadiene was then introduced into the bottle so as to cleanse the medium of the impurities and so as to play the role of transfer agent for the control of the molar masses of the polymer.

A "polymerization solvent (methylcyclohexane)/monomer (butadiene)" weight ratio of 9 was used.

The [Nd/butadiene/HDiBA/CDEA] catalyst prepared previously was introduced into the bottle in an amount of 192 µmol of neodymium per 100 g of butadiene. This is the value of the catalytic base.

The bottle was then placed in a thermostated bath at the desired temperature of 90° C.

1 ml of methanol was used to stop the polymerization reactions.

The polybutadienes were then extracted from the polymer solutions thus obtained, either by steam stripping and drying on rolls at 100° C. or drying in an oven at 60° C. under vacuum with a slight stream of nitrogen, or by devolatilization by drawing the vacuum under nitrogen at 60° C.

The key parameters are the polymerization kinetics and the molar mass distribution of the elastomers obtained, and also the content of cis-1,4 units. The measurement of the degree of conversion of the monomer to polymer as a function of the reaction time is used to describe the polymerization kinetics. This degree of conversion is determined by the solids content technique. The characterization of the macrostructure of the polymers was carried out by the SEC method. The characterization of the microstructure of the polymers was carried out by the "near infrared" (NIR) method.

The test results are summarized in Table 2 below:

TABLE 2

| TEST | Molar ratios of the Nd/Bd/HDiBA/CDEA catalyst system | % conversion (time in min.) | $\eta_{inh}$ (dl/g) | Mn in g/mol ($I_P$) | cis-1,4 content |
|---|---|---|---|---|---|
| With the Nd salt of Ex. 1 | 1/30/3.5/2.9 | 100 (30) | 2.03 | 117 000 (1.77) | 97.0 |
| With the Nd salt of Ex. 2 | 1/30/3.5/2.9 | 100 (30) | 2.10 | 114 000 (1.74) | 97.9 |
| Control "3.5" | 1/30/3.5/2.9 | 100 (30) | 2.13 | 177 000 (1.77) | 98.0 |

Furthermore, the catalytic activity of these catalyst systems was also evaluated. Measured by conversion, it is represented in Table 3 below:

TABLE 3

| % conversion | Control | Example 1 | Example 2 |
|---|---|---|---|
| After 5 min | 71% | 78% | 69% |
| After 10 min | 93% | 95% | 92% |
| After 15 min | 97% | 99% | 95% |

The results of the tests show that the solutions prepared via a direct pathway according to the synthesis process of the invention can be used as is for the preparation of catalysts that are effective for the cis-1,4 stereospecific polymerization of butadiene.

The kinetics of the polymerizations are equivalent or even slightly superior to those observed with a catalyst prepared from a control commercial gel. The molecular weight distributions are narrow, as shown by the values of the polydispersity index, which are all below 2. The polybutadienes formed have a content of cis-1,4 units that is high and greater than 97%.

APPENDIX 1

Measurement of the Intrinsic Viscosity

The intrinsic viscosity ηinh is measured at 25° C. at 0.1 g/dL in toluene and characterizes the macrostructure of the elastomer.

The viscosity is calculated from the equation:

$$\eta = \frac{1}{C} \times \ln\left(\frac{T_1}{T_2}\right)$$

where η is the intrinsic viscosity (dL/g), C the concentration of polymer in toluene (g/dL), T1 the flow time of the polymer solution (s) and T2 the flow time of the toluene (s).

Characterization of the Macrostructure by SEC a) Measurement Principle:

Size exclusion chromatography (SEC) makes it possible to physically separate the macromolecules according to their size in the swollen state through columns filled with a porous stationary phase. The macromolecules are separated according to their hydrodynamic volume, those with the largest volumes being eluted first.

Without being an absolute method, SEC allows the molecular weight distribution of a polymer to be assessed. The various number-average ($M_n$) and weight-average ($M_w$) molecular weights may be determined, and the polydispersity index ($I_p = M_w/M_n$) calculated, from commercial standards.

b) Preparation of the Polymer:

There is no particular treatment of the polymer sample before analysis. It is simply dissolved in tetrahydrofuran at a concentration of around 1 g/l.

c) SEC Analysis:

Case c1) The equipment used is a WATERS Alliance chromatograph. The eluting solvent is tetrahydrofuran, the flow rate is 1 ml/min, the temperature of the system is 35° C. and the analysis time is 90 min. A set of two columns having the trade name STYRAGEL HT6E is used.

The injected volume of the polymer sample solution is 100 μl. The detector is a WATERS 2140 differential refractometer and the software for processing the chromatographic data is the WATERS Millennium system.

Case c2) The equipment used is a WATERS model 150C chromatograph. The eluting solvent is tetrahydrofuran, the flow rate is 0.7 ml/min, the temperature of the system is 35° C. and the analysis time is 90 min. A set of four columns in series is used, the columns having the trade names SHODEX KS807, WATERS STYRAGEL HMW7 and two WATERS STYRAGEL HMW6E.

The injected volume of the polymer sample solution is 100 μl. The detector is a WATERS model RI32X differential refractometer and the software for processing the chromatographic data is the WATERS MILLENNIUM system (version 3.00).

Characterization of the Microstructure (cis-1,4 Content) by Near-Infrared (NIR)

The "near-infrared" (NIR) assay technique was used. This is an indirect method requiring "control" elastomers whose microstructure has been measured by the $^{13}$C NMR technique. The quantitative relationship (Beer-Lambert law) that exists between the distribution of monomers in an elastomer and the shape of the elastomer NIR spectrum is used. This technique is carried out in two steps:

1) Calibration:

The respective spectra of the "control" elastomers were acquired. A mathematical model is established that associates one microstructure with a given spectrum, this being done using the method of partial least squares (PLS) regression that is based on a factorial analysis of the spectral data. The following two documents relate, in an in-depth manner, to the theory and use of this method for analysing "multivariant" data:

(1) P. GELADI and B. R. KOWALSKI, "Partial Least Squares regression: a tutorial", Analytica Chimica Acta, vol. 185, 1-17 (1986).

(2) M. TENENHAUS, "La régression PLS—Théorie et pratique" [PLS regression—theory and practice], Paris, Editions Technip (1998).

2) Measurement:

The spectrum of the sample was recorded. Then the microstructure was calculated.

The invention claimed is:

1. A process for the synthesis of a rare-earth organophosphate comprising:
dispersing, under high shear, in a mixer having agitator impellers, a rare-earth oxide in a two-phase medium comprising at least one organic solvent, water, an organophosphoric acid and an organic or mineral acid and, simultaneously or sequentially,
reacting the rare-earth oxide with the organophosphoric acid and the organic or mineral acid,
wherein the two-phase medium is driven, during the dispersion, by a shear rate of greater than 200 s$^{-1}$, expressed by the equation:

$$\delta_{average} = kN$$

in which k is a constant ranging from 10 to 13 and N is the rotation speed of the agitator impellers expressed in s$^{-1}$, by a blade tip peripheral speed of greater than 4 m/s, expressed by the equation:

$$V_{periph} = \pi ND$$

in which D is the diameter of the agitator impellers expressed in meters and N is their rotational speed expressed in s$^{-1}$
wherein the organic or mineral acid is selected from the group consisting of perchloric acid HClO$_4$, chloric acid HClO$_3$, chlorous acid HClO$_2$, hydrochloric acid HCl, bromic acid HBrO$_3$, hydrobromic acid HBr, iodic acid HIO$_3$, periodic acid HIO$_4$, orthoperiodic acid H$_5$IO$_6$, hydroiodic acid HI, trichloroacetic acid CCl$_3$—COOH, dichloroacetic acid CCl$_2$H—COOH, trifluoroacetic acid CF$_3$COOH, nitric acid HNO$_3$, peroxonitric acid HNO$_4$, sulphurous acid H$_2$SO$_3$, sulphuric acid H$_2$SO$_4$, lithium, sodium or potassium hydrogen sulphates, fluorosulphuric acid FSO$_3$H, sulphonic acid HSO$_3$H, trifluoromethanesulphonic acid CF$_3$—SO$_3$H$_4$, benzenesulphonic acid, naphthalenesulphonic acid, phosphoric acid H$_3$PO$_4$, lithium, sodium or potassium hydrogen phosphates, pyrophosphoric acid H$_4$P$_2$O$_7$, phosphorous acid H$_3$PO$_3$, hypophosphorous acid H$_3$PO$_2$, chromic acid H$_2$CrO$_4$, picric acid, maleic acid, oxalic acid, and mixtures thereof.

2. The process for the synthesis of a rare-earth organophosphate according to claim 1, wherein the medium is driven, during the dispersion, by a shear rate between 200 s$^{-1}$ and 50 000 s$^{-1}$.

3. The process for the synthesis of a rare-earth organophosphate according to claim 1, wherein the blade tip peripheral speed is between 10 m·s$^{-1}$ and 50 m·s$^{-1}$.

4. The process for the synthesis of a rare-earth organophosphate according to claim 1, wherein the rare-earth oxide is chosen from lanthanide oxides.

5. The process for the synthesis of a rare-earth organophosphate according to claim 4, wherein the rare-earth oxide is neodymium oxide.

6. The process for the synthesis of a rare-earth organophosphate according to claim 1, wherein the rare-earth oxide has a degree of hydration between 0 and 25%.

7. The process for the synthesis of a rare-earth organophosphate according to claim 1, wherein the organophosphoric acid is selected from the group consisting of phosphoric acid diesters of formula (RO)(R'O)PO(OH), wherein R is an n-butyl, isobutyl, pentyl, amyl, isopentyl, 2,2-dimethylhexyl, 2-ethylhexyl, 1-ethylhexyl, tolyl, nonylphenoxy radical and R' is an n-butyl, isobutyl, pentyl, amyl, isopentyl, 2,2-dimethylhexyl, 2-ethylhexyl, 1-ethylhexyl, tolyl, nonylphenoxy radical; phosphoric acid monoesters of formula (RO)PO(OH)$_2$ wherein R is an n-butyl, isobutyl, pentyl, amyl, isopentyl, 2,2-dimethylhexyl, 2-ethylhexyl, 1-ethylhexyl, tolyl, nonylphenoxy radical; phosphonates of formula (RO)R'P(O) or RP(O)(OH)$_2$ wherein R is an n-butyl, isobutyl, pentyl, amyl, isopentyl, 2,2-dimethylhexyl, 2-ethylhexyl, 1-ethylhexyl, tolyl, nonylphenoxy radical; phosphinates of formula R(R')P(O)OH or R(H)P(O)OH wherein R is an n-butyl, isobutyl, pentyl, amyl, isopentyl, 2,2-dimethylhexyl, 2-ethylhexyl, 1-ethylhexyl, tolyl, nonylphenoxy radical; and mixtures thereof.

8. The process for the synthesis of a rare-earth organophosphate according to claim 7, wherein the organophosphoric acid is a phosphoric acid diester.

9. The process for the synthesis of a rare-earth organophosphate according to claim 8, wherein the organophosphoric acid is di(2-ethylhexyl)phosphoric acid.

10. The process for the synthesis of a rare-earth organophosphate according to claim 8, wherein the molar ratio of the phosphoric acid diester to the rare earth is from 2.8 to 3.3.

11. The process for the synthesis of a rare-earth organophosphate according to claim 1, wherein the organic or mineral acid is selected from the group consisting of hydrochloric acid HCl, trichloroacetic acid CCl$_3$—COOH, trifluoroacetic acid CF$_3$COOH, nitric acid HNO$_3$, sulphuric acid H$_2$SO$_4$, lithium, sodium or potassium hydrogen sulphates, trifluoromethanesulphonic acid CF$_3$—SO$_3$H, phosphorous acid H$_3$PO$_3$ or hypophosphorous acid H$_3$PO$_2$, and mixtures thereof.

12. The process for the synthesis of a rare-earth organophosphate according to claim 11, wherein the mineral acid is selected from the group consisting of hydrochloric acid HCl and nitric acid HNO$_3$.

13. The process for the synthesis of a rare-earth organophosphate according to claim 1, wherein the molar ratio of the organic or mineral acid to the rare earth is between 0 and 0.25.

14. The process for the synthesis of a rare-earth organophosphate according to claim 1, wherein the molar ratio of the sum of the amount of organophosphoric acid and the amount of organic or mineral acid with respect to the rare earth is between 2.7 and 4.25.

15. The process for the synthesis of a rare-earth organophosphate according to claim 1, wherein the organic solvent is an inert hydrocarbon solvent selected from the group consisting of n-pentane, cyclopentane, cyclohexane, methylcyclohexane, and mixtures thereof.

16. The process for the synthesis of a rare-earth organophosphate according to claim 1, wherein the volume ratio of water relative to the organic solvent is greater than 0 and less than 1.

17. The process for the synthesis of a rare-earth organophosphate according to claim 1, wherein it takes place, in its entirety, within a single reactor.

18. The process for the synthesis of a rare-earth organophosphate according to claim 1, wherein it is carried out successively in a first reactor that is suitable for the dispersion, under high shear, of the rare-earth oxide in the medium, then in a second reactor, into which the reaction mixture obtained in the first reactor is decanted, in order to continue the process.

19. The process for the synthesis of a rare-earth organophosphate according to claim 1, further comprising, after the step of reacting the rare-earth oxide with the organophosphoric acid and the organic or mineral acid, removing water by azeotropic distillation.

20. The process for the synthesis of a rare-earth organophosphate according to claim 1, wherein, once the synthesis of the rare-earth organophosphate has been carried out, the process does not comprise a subsequent step of treating generated effluents.

21. The process for the synthesis of a rare-earth organophosphate according to claim 1, further comprising, once the synthesis of the rare-earth organophosphate has been carried out, recycling the effluents of the reaction possibly containing unreacted organophosphoric acid upstream of the process.

22. Neodymium organophosphate in solution, having at least one of the following characteristics:
a weight content of Nd of between 2.2 and 8.5%,
a residual acidity in the solution of between 0 and 25 mmol per 100 g of salt,
a viscosity of the solutions of between 1000 and 20 000 cP,
wherein the neodymium organophospate is produced by the process according to claim 1.

23. Neodymium organophosphate in solution, having at least one of the following characteristics:
a weight content of Nd of between 2.3 and 8%,
a residual acidity in the solution of between 1 and 15 mmol per 100 g of salt,
a viscosity of the solutions of between 1000 and 20 000 cP,
wherein the neodymium organophospate is produced by the process according to claim 1.

24. The neodymium organophosphate in solution according to claim 22, having a molar ratio of free organophosphoric acid to neodymium ranging from 0 to 30%.

25. A process for the preparation of a "preformed" catalyst system for the stereospecific polymerization of conjugated dienes based on at least
a conjugated diene monomer,
the rare-earth organophosphate,
an alkylating agent constituted of an alkylaluminium of formula AlR$_3$ or HalR$_2$ and
a halogen donor which belongs to the family of alkylaluminium halides with the exclusion of alkylaluminium sesquihalides,
comprising preparing a rare-earth organophosphate as defined in claim 1.

26. The process according to claim 25, wherein the rare-earth organophosphate is a lanthanide organophosphate.

27. The process according to claim 26, wherein the lanthanide organophosphate is neodymium tris[di(2-ethylhexyl) phosphate].

* * * * *